United States Patent [19]

Cavazza

[11] 4,194,006

[45] Mar. 18, 1980

[54] THERAPEUTIC APPLICATION OF ACETYL-d,l-CARNITINE AND OTHER ACYL DERIVATIVES OF D,L-CARNITINE

[76] Inventor: Claudio Cavazza, via Marocco 35, Rome, Italy, 00144

[21] Appl. No.: 895,044

[22] Filed: Apr. 10, 1978

[30] Foreign Application Priority Data

Apr. 29, 1977 [IT] Italy ............................ 49180 A/77
Feb. 3, 1978 [IT] Italy ............................ 47898 A/78

[51] Int. Cl.$^2$ ...................... A61K 31/22; A61K 31/23
[52] U.S. Cl. ...................... 424/311; 424/312; 424/314
[58] Field of Search ...................... 424/311, 312

[56] References Cited

PUBLICATIONS

Strack et al., Chem. Abst., vol. 85 (1976), p. 186,608n.
Hosein et al., J. of Pharmacol. and Exptl. Therapeutics, vol. 156 (1967) pp. 565–572.
Grollman, Pharmacology and Therapeutics, sixth edition (1965), pp. 357 & 358.

*Primary Examiner*—Sam Rosen
*Attorney, Agent, or Firm*—McGlew and Tuttle

[57] ABSTRACT

Certain methods of using acyl derivatives of d,l-carnitine have been provided in therapy of myocardial anoxia, ischaemia, arrhythmic syndromes and heart failure in both animals and in man. Acetyl-d,l-carnitine and its pharmaceutically acceptable salts, e.g., the hydrochloride salt, have shown a remarkable improvement in therapy of heart fatigue in animals and humans, and in pathological situations characterized by cardiac rhythm disorders. Other very effective carnitine derivatives are: propionyl d,l-carnitine, butyryl-d,l-carnitine, hydroxybutyryl d,l-carnitine, hexanoyl d,l-carnitine, octanoyl d,l-carnitine, decanoyl d,l-carnitine, palmitoyl d,l-carnitine, stearoyl d,l-carnitine, and acetoacetyl d,l-carnitine.

16 Claims, No Drawings

THERAPEUTIC APPLICATION OF ACETYL-D,L-CARNITINE AND OTHER ACYL DERIVATIVES OF D,L-CARNITINE

BACKGROUND OF THE INVENTION

1. Field of the Invention

The present invention refers to a new therapeutic application of acetyl-d,l-carnitine and other acyl derivatives of d,l-carnitine which are used as such or as pharmacologically acceptable salts in the therapy of myocardial anoxia, ischaemia, arrhythmic syndromes and heart failure, as well as in all those cases where the energy requirement of the heart increases due to fatigue. These acyl d,l-carnitine derivatives are also useful in protecting against adrenalin toxicity. They are remarkably superior to d,l-carnitine in respect to all these pharmacological actions.

2. Prior Art

The use of d,l-carnitine is well known especially in paediatrics for the treatment of lipid metabolism affections and in the dystrophic type muscular affections. Recently, d,l-carnitine has exhibited cardiotropic properties capable of resolving pathological situations characterized by cardiac rhythm disorders.

Moreover oxygen consumption in heart homogenates in the presence of acetyl-d,l-carnitine is markedly greater than oxygen consumption in the presence of d,l-carnitine and is independent from CoA additions (Table 1).

d,l-Carnitine and its use for treating heart failure have been described in U.S. Pat. Nos. 3,830,931 and 3,968,241. Esters of d,l-carnitine are also known to have physiological activity, and in particular have been found to excite contraction in the frog heart, as described in the German Pat. No. 719891. The pharmacological action of carnitine and its esters is known and described in the literature, e.g., Robert S. Harris et al, *Vitamins and Hormones*, Volume XV, Academic Press, Inc., 1957, pages 73–118. However, nothing in the literature has been found to disclose the remarkable increase in therapeutic properties of the particular esters of carnitine according to the present invention.

DESCRIPTION OF THE INVENTION

The present invention is the result of a pharmacological investigation for the purpose of comparing the cardiotropic properties possesed by d,l-carnitine with the following acyl derivatives of d,l-carnitine: acetyl-d,l-carnitine, propionyl-d,l-carnitine, butyryl-d,l-carnitine, hydroxy-butyryl-d,l-carnitine, hexanoyl-d,l-carnitine, octanoyl-d,l-carnitine, decanoyl-d,l-carnitine, palmitoyl-d,l-carnitine, stearoyl-d,l-carnitine and acetoacetyl-d,l-carnitine.

The results of this investigation are seen from a comparison of the pharmacological activity of d,l-carnitine with respect to cardiotropic properties and in the therapy of anoxia, ischaemia, heart failure and arrhythmic syndromes.

The method of preparing acetyl-d,l-carnitine has already beem amply described by Erich Strack et al in *Chem. Ber.* 86, 525-9 (1953). With regard to the acyl derivatives of d,l-carnitine various researchers have contrived processes for the esterification of the hydroxyl group of γ-trimethyl amino β-hydroxy butyric acid (carnitine), with fatty acids having a more or less long linear chain. See, for example, G. Fraenkel and S. Friednam, *Vitamins Hormones* 15 (1957) 491; J. Bremer, *J. Biol. Chem.* 273 (1962) 2228; and I. B. Fritz, et al, *J. Lipid Res.* 4 (1963) 279.

As has been stated hereinabove, the d,l-carnitine derivatives are esters of γ-trimethylamino-β-hydroxybutyric acid, the esters being formed by acylation of the β-hydroxy group. These derivatives are used therapeutically in the d,l-form without resolution into the separate d- and l- forms of optical isomers. Nevertheless, it is contemplated that they might be so used, although in such case, the l-form of isomer would be preferred.

The improvement in therapeutic action of these ester derivatives of d,l-carnitine is remarkable in both animals and in humans. Clinical studies bear out the indications of surprisingly greater activity described in the animal data summarized hereinbelow.

SUMMARY AND OBJECTS OF THE INVENTION

According to the present invention, a method of therapy for animals and humans is provided for treatment of heart failure due to fatique where the energy requirement of the heart is increased for various reasons. Thus, it is an object of the present invention to provide an improved method of treating heart failure due to increased energy requirements of the heart brought on by fatigue and in therapy of mycardial anoxia, ischaemia, and arrhythmic syndromes of the animal or human heart.

According to the invention, a d,l-carnitine ester derivative is used for administration to the animal or human with the following formula:

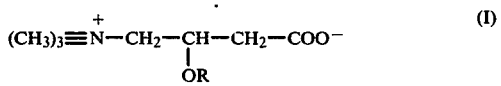

wherein R represents acetyl, propionyl, butyryl, hydroxybutyryl, hexanoyl, octanoyl, decanoyl, palmitoyl, stearoyl and acetoacetyl. Also, pharmaceutically acceptable salts of (I) are useful; for example the hydrochloride salts of (I) are particularly useful.

These d,l carnitine derivatives and their salts are administered intraperitoneally, intravenously, perorally, intramuscularly, by inhalation or by suppository. Suitable dosage forms, such as tablet, capsule, solutions and suspensions are useful, as will be more fully discussed and illustrated by example hereinbelow.

In the following illustrative examples, parts and percentages are by weight, unless otherwise indicated and temperatures are in degrees Centigrade. The relationship of parts by weight to parts by volume is that of grams to milliliters unless otherwise indicated. The examples are for illustration only, and are not to be construed as limiting the scope of the invention.

EXAMPLES

EXAMPLE I

Therapeutic Applications of Acyl d,l-carnitine Derivatives

The tolerance of acetyl-d,l-carnitine and of the other aforementioned acyl derivatives of the formula (I), as well as their salts were investigated by comparing the $LD_{50}$ obtained by administering the compounds intravenously in mice with the $LD_{50}$ obtained under the same experimental conditions by intravenous injection of d,l-carnitine. As indicated by the $LD_{50}$ values given in Table 2 below, acetyl-d,l-carnitine exhibits greater tolerance than that displayed by d,l-carnitine. Also all the other acyl derivatives of d,l-carnitine of the formula (I) display excellent tolerance.

The cardiokinetic effect on isolated heart was also investigated as follows. Rabbit hearts isolated by the Langendorff method were perfused with oxygenized ringer solution at 38.2° C. The isometric contractions, electrocardiogram and coronary flow were recorded using a "Battaglia-Rangoni" polygraph. By removing the oxygen from the perfusion fluid, metabolic damage was induced in the cardia muscle, up to an 80% reduction in the cardiac contractile force.

Under these conditions of prolonged anoxia the aerobic glycolysis of the myocardium is slowed down, accompanied by the storage of acid catabolites due to both the accumulation of pyruvic acid and its conversion to lactic acid which cannot be utilized because of the depression of pyridine enzymes, such as LDH (lactodehydrogenase). This has repercussions on the anaerobic glycolysis affecting an ever increasing number of enzymes, accompanied by a progressive and increasingly critical exhaustion of the myocardium. Thus a whole series of cardiac muscle fatigue levels occurs which can be observed by the behavior of the examined parameters, namely the contractile force, coronary flow, heart rate and cardiac rhythm. As soon as the contractile force was reduced by 80%, the perfusion fluid was once again oxygenized either without adding other compounds (controls) or with the addition of the compounds under examination.

Table 3 below gives the percentage values of the contractile force of the heart, showing a positive inotropic effect, calculated after 10 minutes from the interruption of the anoxic period (myocardial restoration).

The results, evaluated by means of Student's "t" test, show that at equal concentrations in the perfusion fluid, acetyl-d,l-carnitine, propionyl-d,l-carnitine, butyryl-d,l-carnitine, hydroxy-butyryl-d,l-carnitine and acetoacetyl-d,l-carnitine induce a greater positive inotropic effect than that induced by d,l-carnitine and by the other compounds under examination, with statistically significant differences as compared with the controls.

The coronary vasodilator effect was also investigated with the results described herein below. Table 4 shows the coronary flow percentage values. All the compounds of formula (I) under examination provoke, as compared with controls, a small statistically non-significant increase in coronary flow.

The chronotropic effect was examined, and all the compounds of the formula (I) under examination did not significantly change heart rate versus controls.

The antiarrhythmic effect was also investigated and it was found that by using the isolated rat atrium method described by M. Libonati and G. Segre, among the compounds of the formula (I) under examination, acetyl-d,l-carnitine, butyryl-d,l-carnitine and hydroxy-butyry-d,l-carnitine are especially useful since they possess the most clear cut antiarrhythmic properties. These results are shown in table 5 hereinbelow.

The antifatigue effect was also examined with the following results. The antifatigue effect was investigated by administering the compounds of the formula (I) according to the present application to female rats intraperitoneally in saline solution and saline solution alone to the controls by the same route. Every 15 minutes (sessions) after treatment, the animals were placed on a 6 cm diameter rod, rotating at 16 r.p.m. The percentage of the animals capable of staying on the rota-rod for a duration of more than 180 seconds was then recorded. Table 6 gives the percentage values, session by session. The results, assessed by means of the $X^2$ test, show that acetyl-d,l-carnitine possesses a significantly greater antifatigue effect than that displayed by the other compounds under examination.

The antagonism to adrenaline-induced toxicity was also investigated with the following results. Groups of ten male albino Swiss mice were injected with adrenaline (tartrate) intraperitoneally at progressive logarithmic doses. Other similar groups of animals were injected with 250 mg/kg of the compounds under examination via the same route, 30 minutes before adrenaline administration. Mortality was assessed by means of the Litchfield and Wilcoxon method 36 hours after adrenaline administration. The results showed that acetyl-d,l-carnitine, propionyl-d,l-carnitine, butyryl-d,l-carnitine, hydroxy-butyryl-d,l-carnitine and acetoacetyl-d,l-carnitine antagonize adrenaline-induced toxicity to a greater degree than d,l-carnitine, with statistically significant differences.

These results are shown in table 7 hereinbelow.

Further, in view of the aforementioned experimental data it is clear that acetyl-d,l-carnitine, propionyl-d,l-carnitine, butyryl-d,l-carnitine, hydroxy-butyryl-d,l-carnitine and aceto-acetyl-d,l-carnitine exhibit better tolerance properties and greater pharmacological activities with regard to the heart as compared with d,l-carnitine and the other above-mentioned acyl derivatives. Therefore, of all the previously mentioned compounds and their salts, acetyl-d,l-carnitine, propionyl-d,l-carnitine, butyryl-d,l-carnitine, hydroxy-butyryl-d,l-carnitine and acetoacetyl-d,l-carnitine and their pharmaceutically acceptable salts are the most preferred in the therapy of heart diseases of the anoxic, ischaemic, arrhythmic and cardiotoxic types, as well as in those cases where the energy requirement of the heart increases due to fatigue.

EXAMPLE II

1. Solution or sterile aqueous suspension containing acetyl-d,l-carnitine or any one of the derivatives under examination in concentrations from 50 mg to 500 mg per ml.

(a) The excipient for injectable ampoules/vials and for "ready use" syringes is prepared in accordance with the following non-limitative composition:

| | |
|---|---|
| sodium carboxymethyl cellulose (at low viscosity) | 10 mg/ml |
| polysorbate 80 | 4 mg/ml |
| propylparaben | 0.4 mg/ml |
| water for injections sufficient for 1 ml, 2 ml, 5 ml and 10 ml ampoules/vials | |

(b) The excipient for phleboclysis bottles containing 50 ml, 100 ml, 250 ml, 500 ml and 1000 ml is prepared in accordance with the following non-limitative composition:

| | |
|---|---|
| NaCl | 8.6 g/lt |
| KCl | .3 g/lt |
| $CaCl_2$ | .33 g/lt |
| water for injections sufficient for 1 liter. | |

(c) The excipient for bottles for oral use containing from 5 ml to 100 ml is prepared in accordance with the following non-limitative composition:

| | |
|---|---|
| mannitol | 11 mg/ml |
| sorbitol | 600 mg/ml |
| sodium benzoate | 3 mg/ml |
| orange extract | 200 mg/ml |
| vitamin $B_{12}$ | 3 mcg/ml |
| sufficient purified water | |

2. Tablets containing from 20 mg to 500 mg of acetyl-d,l-carnitine or any one of the derivatives under examination. The excipient is prepared in accordance with the following non-limitative composition:

| | |
|---|---|
| starch | 45% |
| avicol | 45% |
| talc | 10% |

3. Capsules containing from 20 mg to 500 mg of acetyl-d,l-carnitine or any one of the derivatives under examination, without excipients in a non-limitative sense.

4. Aerosol and spray preparations from 50 mg to 10 g of acetyl-d,l-carnitine or any one of the derivatives under examination. The excipient is prepared in accordance with the following non-limitative composition:

| | |
|---|---|
| ethanol | 30% |
| purified water | 30% |
| sufficient freon 12/114 (50 parts/50 parts). | |

Table 1

| Concentrations of added CoA | Q $O_2$ ($\mu O_2$/mg protein/hr.) | | |
|---|---|---|---|
| | Control | d,l-carnitine ($10^{-3}$ M) | acetyl-d,l-carnitine ($10^{-3}$ M) |
| 0 | 9.1 | 7.0 | 24.3 |
| $8 \times 10^{-7}$ M | 9.0 | 8.1 | 23.6 |
| $2 \times 10^{-6}$ M | 8.7 | 8.4 | 23.6 |
| $4 \times 10^{-6}$ M | 9.2 | 19.5 | 24.8 |

Table 2

| | Approx. $LD_{50}$ mg/kg intravenously in mice |
|---|---|
| d,l-carnitine | 610 |
| acetyl-d,l-carnitine | 770 |
| propionyl-d,l-carnitine | 761 |
| butyryl-d,l-carnitine | 742 |
| hydroxy-butyryl-d,l-carnitine | 745 |
| hexanoyl-d,l-carnitine | 695 |
| octanoyl-d,l-carnitine | 630 |
| decanoyl-d,l-carnitine | 736 |
| palmitoyl-d,l-carnitine | 750 |
| stearoyl-d,l-carnitine | 745 |
| acetoacetyl-d,l-carnitine | 728 |

The compounds were used as hydrochloryde forms.

Table 3

| | Concentration g/lt | Contractile force Mean ± S.E. | Probability |
|---|---|---|---|
| Control | 0 | 26.6 ± 4.86 | — |
| d,l-carnitine | $1 \cdot 10^{-6}$ | 28.4 ± 3.15 | $p > 0.05$ |
| | $5 \cdot 10^{-6}$ | 32.2 ± 2.90 | $p > 0.05$ |
| | $1 \cdot 10^{-5}$ | 50.9 ± 3.01 | $0.02 > p > 0.01$ |
| acetyl-d,l-carnitine | $1 \cdot 10^{-6}$ | 32.5 ± 4.38 | $p > 0.05$ |
| | $5 \cdot 10^{-6}$ | 42.9 ± 6.22 | $0.05 > p > 0.02$ |
| | $1 \cdot 10^{-5}$ | 77.5 ± 3.29 | $p < 0.001$ |
| propionyl-d,l-carnitine | $1 \cdot 10^{-6}$ | 32.0 ± 5.06 | $p > 0.05$ |
| | $5 \cdot 10^{-6}$ | 38.4 ± 4.86 | $0.05 > p > 0.02$ |
| | $1 \cdot 10^{-5}$ | 60.1 ± 3.12 | $0.01 > p > 0.001$ |
| butyryl-d,l-carnitine | $1 \cdot 10^{-6}$ | 30.6 ± 4.51 | $p > 0.05$ |
| | $5 \cdot 10^{-6}$ | 35.6 ± 6.19 | $p > 0.05$ |
| | $1 \cdot 10^{-5}$ | 51.5 ± 5.02 | $0.02 > p > 0.01$ |
| hydroxy-butyryl-d,l-carnitine | $1 \cdot 10^{-6}$ | 30.1 ± 4.62 | $p > 0.05$ |
| | $5 \cdot 10^{-6}$ | 38.6 ± 7.12 | $0.05 > p > 0.02$ |
| | $1 \cdot 10^{-5}$ | 54.3 ± 6.18 | $0.02 > p > 0.01$ |
| hexanoyl-d,l-carnitine | $1 \cdot 10^{-6}$ | 24.2 ± 3.88 | $p > 0.05$ |
| | $5 \cdot 10^{-6}$ | 28.8 ± 3.16 | $p > 0.05$ |
| | $1 \cdot 10^{-5}$ | 38.0 ± 4.80 | $0.05 > p > 0.02$ |
| octanoyl-d,l-carnitine | $1 \cdot 10^{-6}$ | 25.2 ± 3.60 | $p > 0.05$ |
| | $5 \cdot 10^{-6}$ | 29.8 ± 4.13 | $p > 0.05$ |
| | $1 \cdot 10^{-5}$ | 37.8 ± 4.62 | $0.05 > p > 0.02$ |
| decanoyl-d,l-carnitine | $1 \cdot 10^{-6}$ | 26.9 ± 5.02 | $p > 0.05$ |
| | $5 \cdot 10^{-6}$ | 29.1 ± 3.12 | $p > 0.05$ |
| | $1 \cdot 10^{-5}$ | 36.3 ± 6.53 | $p > 0.05$ |
| palmitoyl-d,l-carnitine | $1 \cdot 10^{-6}$ | 27.8 ± 4.71 | $p > 0.05$ |
| | $5 \cdot 10^{-6}$ | 33.4 ± 3.08 | $p > 0.05$ |
| | $1 \cdot 10^{-5}$ | 38.2 ± 4.75 | $0.05 > p > 0.02$ |
| stearoyl-d,l-carnitine | $1 \cdot 10^{-6}$ | 27.1 ± 3.18 | $p > 0.05$ |
| | $5 \cdot 10^{-6}$ | 27.5 ± 4.09 | $p > 0.05$ |
| | $1 \cdot 10^{-5}$ | 32.8 ± 3.01 | $p > 0.05$ |
| acetoacetyl-d,l-carnitine | $1 \cdot 10^{-6}$ | 30.1 ± 3.98 | $p > 0.05$ |
| | $5 \cdot 10^{-6}$ | 38.2 ± 4.66 | $0.05 > p > 0.02$ |
| | $1 \cdot 10^{-5}$ | 58.3 ± 5.08 | $0.01 > p > 0.001$ |

Table 4

| | Concentration g/lt | Coronary flow Mean ± S.E. | Probability |
|---|---|---|---|
| Control | 0 | 82.25 ± 4.25 | — |
| d,l-carnitine | $1 \cdot 10^{-6}$ | 74.02 ± 6.17 | p>0.05 |
| | $5 \cdot 10^{-6}$ | 77.85 ± 3.01 | " |
| | $1 \cdot 10^{-5}$ | 85.18 ± 3.26 | " |
| acetyl-d,l-carnitine | $1 \cdot 10^{-6}$ | 75.80 ± 5.92 | p>0.05 |
| | $5 \cdot 10^{-6}$ | 76.30 ± 11.9 | " |
| | $1 \cdot 10^{-5}$ | 90.05 ± 7.10 | " |
| propionyl-d,l-carnitine | $1 \cdot 10^{-6}$ | 80.61 ± 7.56 | p>0.05 |
| | $5 \cdot 10^{-6}$ | 78.76 ± 11.03 | " |
| | $1 \cdot 10^{-5}$ | 89.27 ± 7.24 | " |
| butyryl-d,l-carnitine | $1 \cdot 10^{-6}$ | 74.01 ± 6.19 | p>0.05 |
| | $5 \cdot 10^{-6}$ | 74.21 ± 8.78 | " |
| | $1 \cdot 10^{-5}$ | 90.12 ± 8.18 | " |
| hydroxy-butyryl-d,l-carnitine | $1 \cdot 10^{-6}$ | 73.12 ± 6.80 | p>0.05 |
| | $5 \cdot 10^{-6}$ | 76.04 ± 8.96 | " |
| | $1 \cdot 10^{-5}$ | 89.19 ± 6.75 | " |
| | $1 \cdot 10^{-5}$ | 89.19 ± 6.75 | " |
| hexanoyl-d,l-carnitine | $1 \cdot 10^{-6}$ | 76.25 ± 4.75 | p>0.05 |
| | $5 \cdot 10^{-6}$ | 75.28 ± 8.36 | " |
| | $1 \cdot 10^{-5}$ | 84.08 ± 5.14 | " |
| octanoyl-d,l-carnitine | $1 \cdot 10^{-6}$ | 76.24 ± 6.13 | p>0.05 |
| | $5 \cdot 10^{-6}$ | 76.00 ± 9.16 | " |
| | $1 \cdot 10^{-5}$ | 84.71 ± 6.20 | " |
| decanoyl-d,l-carnitine | $1 \cdot 10^{-6}$ | 76.30 ± 9.42 | p>0.05 |
| | $5 \cdot 10^{-6}$ | 72.60 ± 12.4 | " |
| | $1 \cdot 10^{-5}$ | 83.21 ± 5.70 | " |
| palmitoyl-d,l-carnitine | $1 \cdot 10^{-6}$ | 78.15 ± 7.21 | p>0.05 |
| | $5 \cdot 10^{-6}$ | 72.20 ± 12.73 | " |
| | $1 \cdot 10^{-5}$ | 84.68 ± 7.20 | " |
| stearoyl-d,l-carnitine | $1 \cdot 10^{-6}$ | 80.21 ± 8.78 | p>0.05 |
| | $5 \cdot 10^{-6}$ | 77.30 ± 11.8 | " |
| | $1 \cdot 10^{-5}$ | 81.05 ± 6.27 | " |
| acetoacetyl-d,l-carnitine | $1 \cdot 10^{-6}$ | 74.65 ± 3.54 | p>0.05 |
| | $5 \cdot 10^{-6}$ | 75.70 ± 10.1 | " |
| | $1 \cdot 10^{-5}$ | 89.82 ± 6.38 | " |

Table 5

| | Mean percent variation versus controls | | | | |
|---|---|---|---|---|---|
| Compound | concentration g/lt | frequency max (−%) | refractory period (+%) | excitability (−%) | rheobase (+%) |
| Quinidine | $1 \cdot 10^{-6}$ | 11.69 | 3.12 | 16.90 | 7.14 |
| | $1 \cdot 10^{-5}$ | 24.06 | 20.38 | 23.44 | 25.06 |
| | $1 \cdot 10^{-4}$ | 71.16 | 57.38 | 189.0 | 54.11 |
| d,l-carnitine | $1 \cdot 10^{-6}$ | 7.28 | 18.33 | 12.72 | 5.81 |
| | $1 \cdot 10^{-5}$ | 23.58 | 25.96 | 19.28 | 9.07 |
| | $1 \cdot 10^{-4}$ | 25.21 | 31.15 | 27.15 | 20.34 |
| acetyl-d,l-carnitine | $1 \cdot 10^{-6}$ | 6.08 | 14.54 | 7.18 | 3.32 |
| | $1 \cdot 10^{-5}$ | 15.00 | 16.82 | 18.59 | 15.28 |
| | $1 \cdot 10^{-4}$ | 23.65 | 27.35 | 71.05 | 21.71 |
| propionyl-d,l-carnitine | $1 \cdot 10^{-6}$ | 10.71 | 8.16 | 2.24 | 3.57 |
| | $1 \cdot 10^{-5}$ | 11.45 | 14.03 | 28.40 | 51.29 |
| | $1 \cdot 10^{-4}$ | 7.65 | 19.33 | 14.68 | 52.08 |
| butyryl-d,l-carnitine | $1 \cdot 10^{-6}$ | 24.81 | 18.18 | 12.89 | 28.28 |
| | $1 \cdot 10^{-5}$ | 30.39 | 25.94 | 31.93 | 40.79 |
| | $1 \cdot 10^{-4}$ | 62.28 | 38.03 | 63.73 | 55.00 |
| hydroxy-butyryl-d,l-carnitine | $1 \cdot 10^{-6}$ | 10.02 | 16.32 | 12.07 | 9.78 |
| | $1 \cdot 10^{-5}$ | 23.20 | 20.31 | 19.12 | 25.35 |
| | $1 \cdot 10^{-4}$ | 42.30 | 27.10 | 63.60 | 42.12 |
| hexanoyl-d,l-carnitine | $1 \cdot 10^{-6}$ | 8.71 | 9.04 | 12.38 | 6.20 |
| | $1 \cdot 10^{-5}$ | 12.28 | 12.70 | 18.16 | 10.12 |
| | $1 \cdot 10^{-4}$ | 25.10 | 21.72 | 26.28 | 21.70 |
| octanoyl-d,l-carnitine | $1 \cdot 10^{-6}$ | 10.92 | 5.73 | 12.65 | 9.46 |
| | $1 \cdot 10^{-5}$ | 36.17 | 16.53 | 28.55 | 0 |
| | $1 \cdot 10^{-4}$ | 17.22 | 39.83 | 47.81 | 4.16 |
| decanoyl-d,l-carnitine | $1 \cdot 10^{-6}$ | 8.66 | 9.14 | 0 | 3.12 |
| | $1 \cdot 10^{-5}$ | 11.96 | 10.31 | 17.21 | 9.54 |
| | $1 \cdot 10^{-4}$ | 24.81 | 21.62 | 25.19 | 21.20 |
| palmitoyl-d,l-carnitine | $1 \cdot 10^{-6}$ | 16.87 | 0 | 0 | 22.18 |
| | $1 \cdot 10^{-5}$ | 8.14 | 13.69 | 3.01 | 7.33 |
| | $1 \cdot 10^{-4}$ | 80.53 | 34.12 | 32.77 | 6.91 |
| stearoyl-d,l-carnitine | $1 \cdot 10^{-6}$ | 0 | 15.61 | 0 | 1.85 |
| | $1 \cdot 10^{-5}$ | 1.92 | 16.22 | 0 | 3.84 |
| | $1 \cdot 10^{-4}$ | 3.50 | 24.63 | 12.30 | 2.08 |
| acetoacetyl-d,l-carnitine | $1 \cdot 10^{-6}$ | 7.34 | 10.70 | 12.16 | 3.01 |
| | $1 \cdot 10^{-5}$ | 22.70 | 14.70 | 27.13 | 9.94 |

Table 5-continued

| Compound | Mean percent variation versus controls | | | | |
|---|---|---|---|---|---|
| | concentration g/lt | frequency max (−%) | refractory period (+%) | excitability (−%) | rheobase (+%) |
| | $1 \cdot 10^{-4}$ | 25.50 | 22.84 | 40.12 | 21.85 |

Table 6

| Compound | no. of rats | mg/kg | sessions every 15 minutes | | | | | |
|---|---|---|---|---|---|---|---|---|
| | | | 1 | 2 | 3 | 4 | 5 | 6 |
| Controls | 20 | 0 | 0 | 0 | 0 | 10.0 | 10.0 | 10.0 |
| | 8 | 0.25 | 0 | 12.5 | 25.0 | 25.0 | 25.0 | 25.0 |
| d,l-amphetamine | 17 | 0.50 | 0 | 5.88 | 11.8 | 23.5 | 29.4 | 35.3 |
| | 12 | 1.00 | 0 | 8.33 | 25.0 | 33.3 | 58.3* | 58.3* |
| | 9 | 200 | 0 | 0 | 0 | 0 | 0 | 0 |
| d,l-carnitine | 10 | 300 | 0 | 0 | 0 | 0 | 10.0 | 10.0 |
| | 12 | 400 | 0 | 0 | 8.33 | 25.0 | 25.0 | 25.0 |
| | 12 | 600 | 0 | 16.7 | 16.7 | 16.7 | 16.7 | 25.0 |
| | 10 | 100 | 0 | 0 | 0 | 0 | 0 | 10.0 |
| acetyl-d,l-carnitine | 10 | 200 | 0 | 0 | 0 | 30.0 | 50.0* | 50.0* |
| | 10 | 400 | 0 | 10.0 | 10.0 | 10.0 | 40.0 | 50.0* |
| | 10 | 600 | 0 | 0 | 10.0 | 20.0 | 40.0 | 50.0* |
| | 10 | 300 | 0 | 0 | 0 | 10.0 | 20.0 | 40.0 |
| propionyl-d,l-carnitine | 10 | 400 | 0 | 0 | 10.0 | 20.0 | 20.0 | 40.0 |
| | 10 | 600 | 0 | 10.0 | 20.0 | 30.0 | 40.0 | 40.0 |
| | 10 | 300 | 0 | 0 | 0 | 0 | 0 | 10.0 |
| butyryl-d,l-carnitine | 10 | 400 | 0 | 0 | 0 | 10.0 | 10.0 | 20.0 |
| | 10 | 600 | 0 | 0 | 10.0 | 20.0 | 20.0 | 40.0 |
| | 10 | 300 | 0 | 0 | 0 | 0 | 10.0 | 20.0 |
| hydroxy-butyryl-d,l-carnitine | 10 | 400 | 0 | 0 | 10.0 | 20.0 | 20.0 | 30.0 |
| | 10 | 600 | 0 | 0 | 10.0 | 20.0 | 30.0 | 40.0 |
| | 10 | 300 | 0 | 0 | 0 | 0 | 10.0 | 10.0 |
| hexanoyl-d,l-carnitine | 10 | 400 | 0 | 0 | 0 | 0 | 10.0 | 10.0 |
| | 10 | 600 | 0 | 0 | 10.0 | 10.0 | 20.0 | 30.0 |
| | 10 | 300 | 0 | 0 | 0 | 0 | 10.0 | 10.0 |
| octanoyl-d,l-carnitine | 10 | 400 | 0 | 0 | 0 | 0 | 10.0 | 10.0 |
| | 10 | 600 | 0 | 0 | 10.0 | 10.0 | 10.0 | 30.0 |
| | 10 | 300 | 0 | 0 | 0 | 10.0 | 10.0 | 10.0 |
| decanoyl-d,l-carnitine | 10 | 400 | 0 | 0 | 0 | 10.0 | 10.0 | 10.0 |
| | 10 | 600 | 0 | 0 | 0 | 10.0 | 10.0 | 20.0 |
| | 10 | 300 | 0 | 0 | 0 | 0 | 10.0 | 10.0 |
| palmitoyl-d,l-carnitine | 10 | 400 | 0 | 0 | 0 | 10.0 | 20.0 | 20.0 |
| | 10 | 600 | 0 | 0 | 0 | 20.0 | 20.0 | 30.0 |
| | 10 | 300 | 0 | 0 | 0 | 10.0 | 10.0 | 10.0 |
| stearoyl-d,l-carnitine | 10 | 400 | 0 | 0 | 0 | 10.0 | 20.0 | 20.0 |
| | 10 | 600 | 0 | 10.0 | 10.0 | 20.0 | 20.0 | 20.0 |
| | 10 | 300 | 0 | 0 | 0 | 10.0 | 10.0 | 10.0 |
| acetoacetyl-d,l-carnitine | 10 | 400 | 0 | 0 | 20.0 | 20.0 | 20.0 | 30.0 |
| | 10 | 600 | 0 | 10.0 | 20.0 | 40.0 | 40.0 | 40.0 |

*statistically significant for $p < 0.05$

Table 7

| Compound | LD$_{50}$mg/kg (fiducial limits for 95%) |
|---|---|
| Adrenaline alone | 27.66 (19.75–38.73) |
| Adrenaline + d,l-carnitine | 103.63 (45.39–236.59) |
| Adrenaline + acetyl-d,l-carnitine | 221.99 (171.92–286.66) |
| Adrenaline + propionyl-d,l-carnitine | 140.21 (85.12–209.37) |
| Adrenaline + butyryl-d,l-carnitine | 187.81 (114.11–224.78) |
| Adrenaline + hydroxy-butyryl-d,l-carnitine | 172.15 (110.02–219.48) |
| Adrenaline + hexanoyl-d,l-carnitine | 108.04 (60.20–212.18) |
| Adrenaline + octanoyl-d,l-carnitine | 106.91 (68.44–208.38) |
| Adrenaline + decanoyl-d,l-carnitine | 116.15 (71.80–210.52) |
| Adrenaline + palmitoyl-d,l-carnitine | 102.98 (52.38–225.41) |
| Adrenaline + stearoyl-d,l-carnitine | 112.74 (85.77–202.18) |
| Adrenaline + acetoacetyl-d,l-carnitine | 203.72 (120.48–264.36) |

What is claimed is:

1. Method of using a composition containing a d,l-carnitine derivative in the therapy of myocardial anoxia, ischaemia, arrhythmic syndromes, and heart fatigue and failure, in animals or in humans which comprises administering an effective dose of said composition to the animal or human for said therapy wherein the d,l-carnitine derivative is (a) a compound of the formula

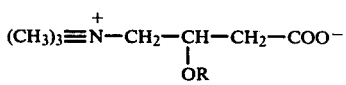

or (b) the pharmaceutically acceptable salts of (I) wherein R represents acetyl, propionyl, butyryl, hydroxy-butyryl, or acetoacetyl.

2. Method according to claim 1, wherein said derivative of d,l-carnitine is acetyl-d,l-carnitine or its pharmacologically acceptable salts.

3. Method according to claim 1 wherein said derivative is propionyl-d,l-carnitine or its pharmacologically acceptable salts.

4. Method according to claim 1 wherein said derivative is butyryl-d,l-carnitine or its pharmacologically acceptable salts.

5. Method according to claim 1 wherein said derivative is hydroxy-butyryl-d,l-carnitine or its pharmacologically acceptable salts.

6. Method according to claim 1 wherein said derivative is acetoacetyl-d,l-carnitine or its pharmacologically acceptable salts.

7. Method according to claim 1 wherein said derivative is administered to humans.

8. Method according to claim 1 wherein said derivative is administered to animals.

9. Method according to claim 1 wherein said derivative is administered per os.

10. Method according to claim 9 wherein said derivative is administered in form of a tablet.

11. Method according to claim 9 wherein said derivative is administered in form of a capsule.

12. Method according to claim 1 wherein said derivative is administered intravenously.

13. Method according to claim 1 wherein said derivative is administered intraperitoneally.

14. Method according to claim 1 wherein said derivative is administered intramuscularly.

15. Method according to claim 1 wherein said derivative is administered buccally.

16. Method according to claim 1 wherein said derivative is administered by suppository.

* * * * *